Dec. 27, 1966 D. L. ARMSTRONG Plant Pat. 2,697
ROSE PLANT
Filed Oct. 7, 1965
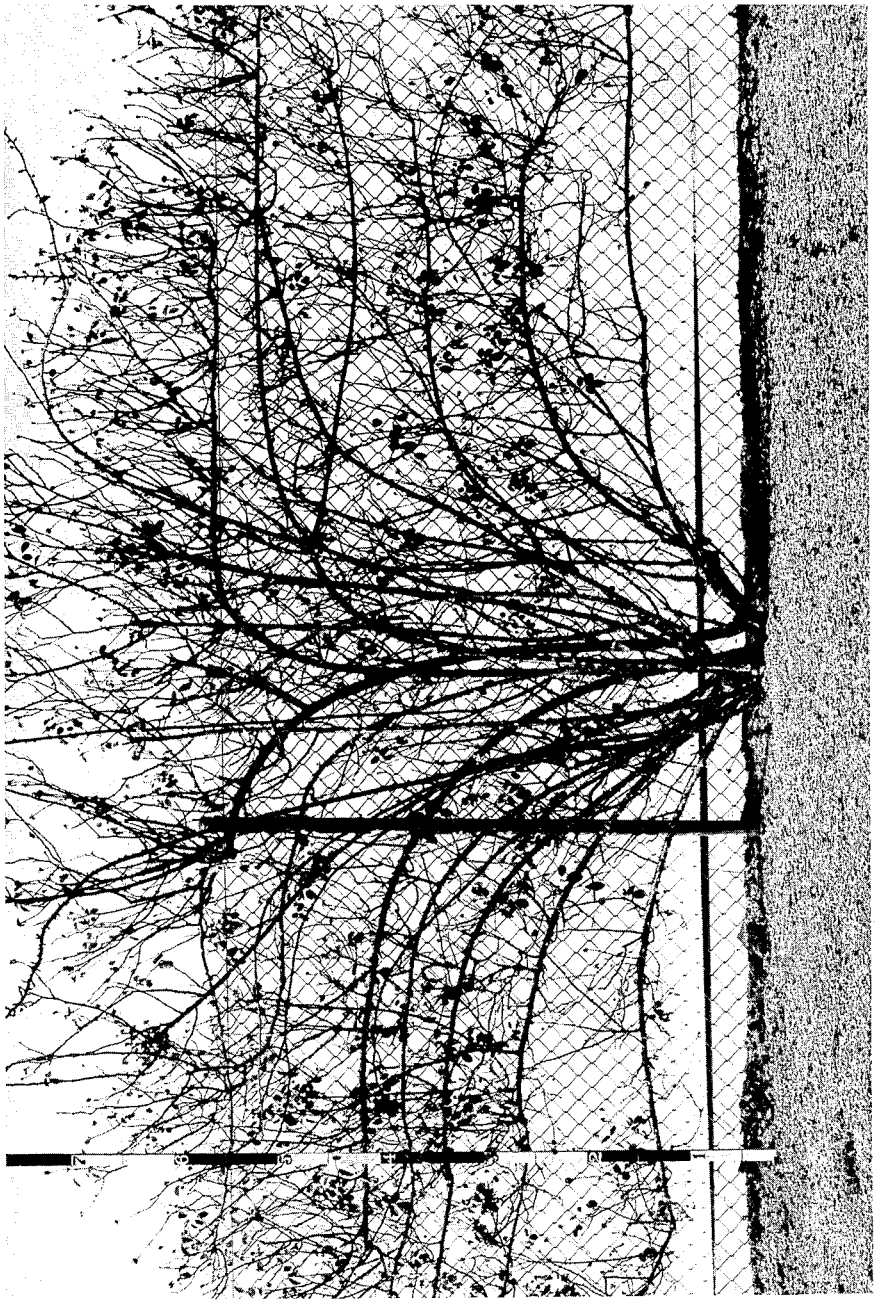
Inventor.
David L. Armstrong
By: Robb & Robb
Attorneys.

United States Patent Office

Plant Pat. 2,697
Patented Dec. 27, 1966

2,697
ROSE PLANT

David L. Armstrong, Ontario, Calif., assignor to Armstrong Nurseries, Inc., Ontario, Calif., a corporation of California Filed Oct. 7, 1965, Ser. No. 493,944
1 Claim. (Cl. Plt.—6)

The present invention relates to a new and distinct variety of rose plant of the climber class, which was discovered by me as a bud sport of the variety known as "El Capitan" (Plant Patent No. 1,796), in the course of a regular research program directed by me in the nurseries of my assignee at Ontario, California.

At the time of my discovery aforesaid, I was inspecting plants of regular bush type rose varieties being grown in the nurseries of my assignee, with the particular purpose of looking for sports. In the course of my inspection, my attention was attracted to one particular plant of the variety "El Capitan" which exhibited an unusual habit of growth, and upon closer observation thereof, I found that it had sported and produced a climbing cane. I thereupon took immediate steps to preserve the sport and to asexually reproduce the same by budding in the nurseries of my assignee, at Ontario, California, finding that the progeny comes true. Continued observations of the original sport and its progency conclusively established that the new sport is substantially identical to its parent, "El Capitan" except for its climbing habit which is evidenced by its long, strong canes which attain a mature length of usually 8 to 10 feet, as distinguished from the low-growing bush form of its parent.

Like climbing sports of other bush varieties, the new variety produces few or no flowers on the current season canes, and rarely a climbing cane will terminate in a flower or a small cluster of flowers, or a cane originating early in the season will produce a few lateral flowering shoots late in the season. This definitely differentiates the sport from the relatively continuous blooming or ever-blooming habit from current season wood which is characteristic of the parent variety "El Capitan."

The new variety repeats blooms heavily or in mass several times a year from previous season canes, with these periods of heavy bloom being separated by intervals of a month or two with little or no bloom.

Being substantially identical in all respects to the parent variety "El Capitan," except for the foregoing general distinctions, it is unnecessary to specifically describe the new sport in detail and the new sport may be considered as otherwise conforming to the detailed description embodied in Plant Patent No. 1,796, issued January 13, 1959, to which reference may be readily had.

For convenience, the accompanying drawing is presented to illustrate the climbing habit of growth of my new variety.

I claim:

A new and distinct variety of rose plant of the climber class, substantially as herein shown and described, characterized particularly as to novelty by being substantially identical to its parent variety "El Capitan" (Plant Patent No. 1796), except for its climbing habit of growth, the production of few or no flowers on current season canes, and the repetition of blooms heavily or in mass several times a year on previous season canes, with these periods of heavy bloom being separated by intervals of little or no bloom.

No references cited.

ABRAHAM G. STONE, *Primary Examiner.*

R. E. BAGWILL, *Assistant Examiner.*